United States Patent [19]

Chorvat

[11] 4,180,666
[45] Dec. 25, 1979

[54] 3,9-DIHYDRO-3,9-DIOXO-2H-INDENO(2,1-C)-PYRIDINE-4-(CARBONITRILES/CARBOXAMIDES)

[75] Inventor: Robert J. Chorvat, Arlington Heights, Ill.

[73] Assignee: G. D. Searle & Co., Skokie, Ill.

[21] Appl. No.: 973,518

[22] Filed: Dec. 26, 1978

[51] Int. Cl.$^2$ .......................................... C07D 221/04
[52] U.S. Cl. ................................. 546/111; 424/263; 424/266
[58] Field of Search ........................................ 546/111

[56] References Cited

PUBLICATIONS

Renfrew, et al., Chem. Abstracts, vol. 86, No. 23, item No. 171,204z, Jun. 6, 1977.

*Primary Examiner*—Alan L. Rotman
*Attorney, Agent, or Firm*—James R. Henes; John M. Brown

[57] ABSTRACT

Preparation and use of anticonvulsant 3,9-dihydro-3,9-dioxo-2$H$-indeno[2,1-c]pyridine-4-(carbonitriles/carboxamides) are disclosed.

12 Claims, No Drawings

3,9-DIHYDRO-3,9-DIOXO-2H-INDENO(2,1-C)-PYRIDINE-4-(CARBONITRILES/CARBOXAMIDES)

This invention relates to 3,9-dihydro-3,9-dioxo-2H-indeno[2,1-c]pyridine-4-(carbonitriles/carboxamides) and processes for the preparation thereof. More particularly, this invention provides new, unobvious, and useful chemical compounds of the formula

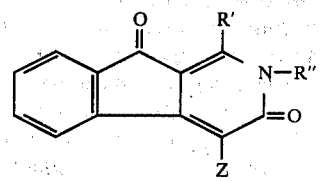

wherein R' represents hydrogen, lower alkyl, or phenyl optionally substituted by one or more lower alkyls; R" represent hydrogen or lower alkyl; and Z represents cyano or carbamoyl.

Those skilled in the art will recognize that "lower alkyl" designates methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, or like monovalent, saturated, acyclic, straight- or branched-chain hydrocarbon groupings of the formula

 $-C_nH_{2n+1}$ wherein n represents a positive integer less than 8, among which lower alkyls containing fewer than 4 carbons are preferred.

The compounds to which this invention relates are useful by reason of their valuable pharmacological properties. Thus, for example, they are anticonvulsants.

The anticonvulsant utility of the instant compounds is evident from the results of a standardized test for their capacity to prevent clonic convulsions induced in mice by pentylenetetrazole. The procedure, a modification of one described by Chen et al., in Proc. Soc. Exp. Biol. and Med., 87, 337 (1954), is as follows: A selected dose (commonly but not invariably 100 mg/kg in the first instance) of the compound to be tested, suspended in 10 ml of a vehicle consisting of approximately 9.8 ml of physiological saline intimately mixed with 0.1 ml of propylene glycol and 0.1 ml of polysorbate 80, is administered intragastrically (IG) or intraperitoneally (IP) to each of a group of 10 male Crl:COBS CD-1(ICR)BR mice weighing 18-28 g apiece. After a selected interval of time (¼, ½, 1, 3, 6, or 24 hr.), each mouse is challenged by intravenous infusion of 35 mg/kg of pentylenetetrazole (sufficient to induce clonic convulsions in control animals) administered as a 0.35% aqueous solution at a rate of approximately 0.1 ml/sec. A compound is considered anticonvulsant at the selected dose if, after the selected time, clonic convulsions are prevented in at least 20% of the animals challenged. The products of Examples 5, 10, and 14 hereinafter (namely, 3,9-dihydro-3,9-dioxo-1-phenyl-2H-indeno[2,1-c]pyridine-4-carbonitrile, 3,9-dihydro-2-methyl-3,9-dioxo-1-phenyl-2H-indeno[2,1-c]pyridine-4carbonitrile, and 3,9-dihydro-3,9-dioxo-1-phenyl-2H-indeno[2,1-c]pyridine-4-carboxamide) were anticonvulsant in this test ½ hr. after IP administration of 60, 100, and 50 mg/kg, respectively. These results are, of course, specified merely for purposes of illustration and, accordingly, are not to be construed as either delimiting or exclusionary.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl esters, talc, stearic acid, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences", 14 Ed., Merck Publishing Company, Eaton, Pa., 1965.

Appropriate dosages, in any given instance, manifestly depend upon the nature and severity of the condition treated, the route of administration, and the species of mammal involved, including its size and any individual idiosyncrasies which obtain.

Preparation of the compounds of this invention proceeds by heating 1,1,3-trichloro-1H-indene [J. Amer. Chem. Soc., 55, 2567 (1933)] in aqueous acetone under nitrogen and contacting the resultant 3-chloro-1H-inden-1-one in N,N-dimethylformamide at −50° C. with 2-sodio-2-cyanoacetamide prepared by contacting 2-cyanoacetamide with sodium hydride in N,N-dimethylformamide. The 2-cyano-2-(3-hydroxy-1H-inden-1-yliden)acetamide which eventuates [or the tautomer thereof, 2-cyano-2-(1-oxo-1H-inden-3-yl)acetamide] is then heated in N,N-dimethylformamide with an orthoalkanoic acid ester of the formula

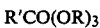 R'CO(OR)₃

[wherein R' is defined as before and R represents methyl or ethyl] to produce the corresponding carbonitrile of this invention having the formula

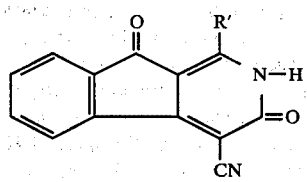

which in turn, is heated in N,N-dimethylformamide with potassium carbonate and a lower alkyl iodide to produce the corresponding carbonitrile of this invention having the formula

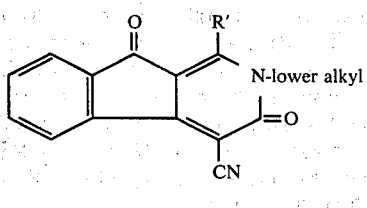

Heating one of the aforesaid carbonitriles with sulfuric acid and a trace of water affords the corresponding carboxamide of this invention, having the formula

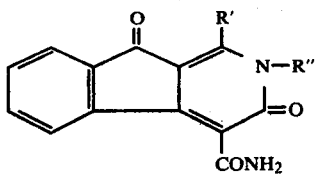

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperature are given in degree centigrade and relative amounts of materials in parts by weight, except as otherwise noted.

EXAMPLE 1

A. A mixture of 35 parts of 1,1,3-trichloro-1H-indene, 295 parts of 2-propanone, and 375 parts of water is heated at the boiling point under reflux in a nitrogen atmosphere overnight. The resultant dark brown solution is stripped of solvent by vacuum distillation under nitrogen at 35°. The distilland is extracted with 1,1'-oxybisethane. The extract is consecutively washed with water, 10% sodium chloride, and water, then dried over anhydrous magnesium sulfate and thereupon stripped of solvent by vacuum distillation. The oily residue is crystallized from pentane to give 3-chloro-1H-inden-1-one as a red-orange solid, the formula of which is

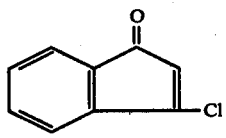

B. Approximately 26 parts of sodium hydride (prepared in a nitrogen atmosphere by washing the oil from 46 parts of 57% dispersion of the hydride in mineral oil) is suspended in 950 parts of N,N-dimethylformamide, and to this suspension is added, portionwise with stirring at room temperature under nitrogen, 82 parts of 2-cyanoacetamide. The resultant mixture is stirred at room temperature for 30 minutes and then cooled to −50°, at which temperature a solution of 80 parts of 3-chloro-1H-inden-1-one in 285 parts of N,N-dimethylformamide is stirred in during 30 minutes. A deep red color develops. Stirring at approximately −50° is continued for a further 30 minutes after addition of the 3-chloro-1H-inden-1-one solution is complete, whereupon 500 parts of acetic acid is stirred in. The resultant solution is allowed to warm to room temperature while 1000 parts of approximately 3.5% hydrochloric acid is mixed in. The red color is concomitantly discharged and a precipitate forms. The precipitate is isolated by filtration; consecutively washed with water, methanol, and 1,1'-oxybisethane; and dried overnight. The material thus obtained is 2-cyano-2-(1-oxo-1H-inden-1-yl)acetamide melting at approximately 221°–222°. This substance has the formula

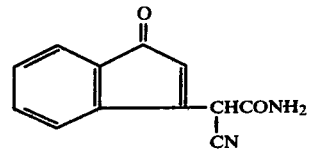

C. A mixture of 3 parts of 2-cyano-2-(3-hydroxy-1H-inden-1-ylidene)acetamide, 3 parts of triethoxymethane, and 19 parts of N,N-dimethylformamide is heated at 90°–95° under reflux for 1 hour, during which a precipitate forms. The resultant mixture is chilled, whereupon the precipitate is filtered out, washed with 1,1'-oxybisethane, and dried in vacuo. The product thus isolated is 3,9-dihydro-3,9-dioxo-2H-indeno[2,1-c]pyridine-4-carbonitrile melting above 300°. The product has the formula

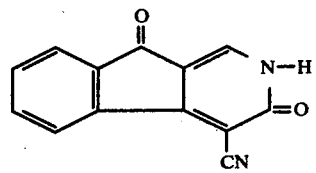

EXAMPLE 2

A mixture of 1 part of 2-cyano-2-(3-hydroxy-1H-inden-1-ylidene)acetamide, 1 part of 1,1,1-triethoxyethane, and approximately 6 parts of N,N-dimethylformamide is heated at 90°–95° under reflux for 2 hours, whereupon the precipitate which forms is filtered out, washed with ethyl acetate, and dried in vacuo. Crystallization from ethyl acetate affords needles of 3,9-dihydro-1-methyl-3,9-dioxo-2H-indeno[2,1-c]pyridine-4-carbonitrile melting above 300°. The product has the formula

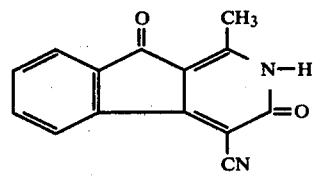

EXAMPLE 3

A mixture of 5 parts of 2-cyano-2-(3-hydroxy-1H-inden-1-ylidene)acetamide, 6 parts of 1,1,1-triethoxypropane, and 75 parts of N,N-dimethylformamide is heated at 90°–95° under reflux for 3 hours, whereupon the precipitate which forms is filtered out, washed with ethyl acetate, and dried in vacuo. The product thus isolated is 1-ethyl-3,9-dihydro-3,9-dioxo-2H-indeno[2,1-c]pyridine-4-carbonitrile, having the formula

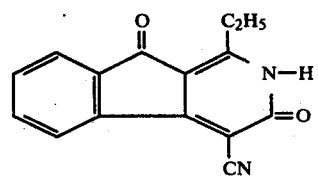

EXAMPLE 4

Substitution of 7 parts of 1,1,1-triethoxy-2-methylpropane for the 1,1,1-triethoxypropane called for in Example 3 affords, by the procedure there detailed, 3,9-dihydro-1-(1-methylethyl)-3,9-dioxo-2H-indeno[2,1-c]pyridine-4-carbonitrile, having the formula

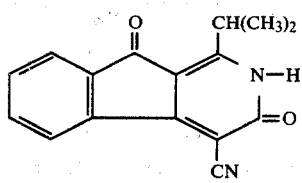

EXAMPLE 5

A mixture of 2 parts of 2-cyano-2-(3-hydroxy-1H-inden-1-ylidene)acetamide, 3 parts of (trimethoxymethyl)benzene, and 29 parts of N,N-dimethylformamide is heated at 100°–105° under reflux for 3¼ hours, whereupon the precipitate which forms is filtered out, consecutively washed with ethyl acetate and 1,1-oxybisethane, and dried in vacuo. The product thus isolated is 3,9-dihydro-3,9-dioxo-1-phenyl-2H-indeno[2,1-c]pyridine-4-carbonitrile melting above 300°. The product has the formula

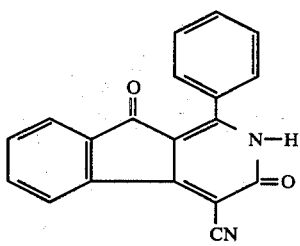

EXAMPLE 6

A mixture of 30 parts of 3,9-dihydro-3,9-dioxo-2H-indeno[2,1-c]pyridine-4-carbonitrile, 228 parts of methyl iodide, 19 parts of potassium carbonate, and 475 parts of N,N-dimethylformamide is heated at 90°–95° for 4 hours, then diluted with 1500 parts of water. The resultant mixture is stirred for 15 minutes, whereupon the yellow precipitate which forms is filtered off, dried in air, and crystallized from a mixture of absolute ethanol and ethyl acetate. The product thus isolated is 3,9-dihydro-2-methyl-3,9-dioxo-2H-indeno[2,1-c]pyridine-4-carbonitrile melting above 300°. The product has the formula

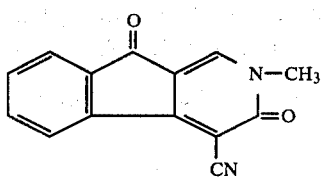

EXAMPLE 7

A mixture of 19 parts of 3,9-dihydro-3,9-dioxo-2H-indeno-[2,1-c]pyridine-4-carbonitrile, 137 parts of 1-iodo-1-methylethane, 15 parts of potassium carbonate, and 475 parts of N,N-dimethylformamide is heated at approximately 60° for 2 hours, then diluted with 1500 parts of water. The precipitate which forms is filtered off, dried in air, and crystallized from a mixture of N,N-dimethylformamide and methanol. The product thus isolated is 3,9-dihydro-2-(1-methylethyl)-3,9-dioxo-2H-indeno[2,1-c]pyridine-4-carbonitrile, having the formula

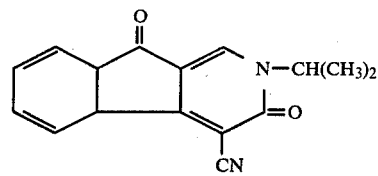

EXAMPLE 8

A mixture of 20 parts of 3,9-dihydro-1-methyl-3,9-dioxo-2H-indeno[2,1-c]pyridine-4-carbonitrile, 114 parts of iodomethane, 15 parts of potassium carbonate, and 475 parts of N,N-dimethylformamide is heated at 55°–60° for 2 hours, then diluted with 1500 parts of water. The precipitate which forms is filtered off, dried in air, and crystallized from a mixture of methanol and N,N-dimethylformamide to give 3,9-dihydro-1,2-dimethyl-3,9-dioxo-2H-indeno[2,1-c]-pyridine-4-carbonitrile melting at 271°–273.5°. The product has the formula

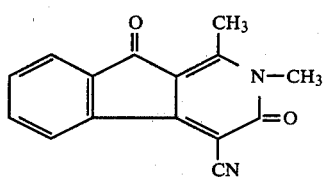

EXAMPLE 9

Substitution of 21 parts of 1-ethyl-3,9-dihydro-3,9-dioxo-2H-indeno[2,1-c]pyridine-4-carbonitrile for the 3,9-dihydro-3,9dioxo-2H-indeno[2,1-c]pyridine-4-carbonitrile called for in Example 7 affords, by the procedure there detailed, 1-ethyl-3,9-dihydro-2-(1-methylethyl)-3,9-dioxo-2H-indeno[2,1-c]pyridine-4-carbonitrile. The product has the formula

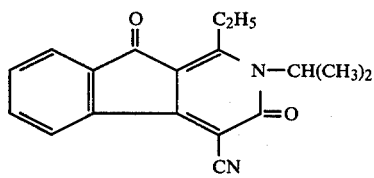

EXAMPLE 10

A mixture of 25 parts of 3,9-dihydro-3,9-dioxo-1-phenyl-2H-indeno[2,1-c]pyridine-4-carbonitrile, 114 parts of iodomethane, 115 parts of potassium carbonate, and 475 parts of N,N-dimethylformamide is heated at 85° for 1¼ hours, then diluted with 1500 parts of water, followed by 100 parts of aqueous 5% sodium hydroxide. The deep tan precipitate which forms is filtered off, dried in air, and consecutively recrystallized from a mixture of chloroform and hexane, ethyl acetate, a mixture of ethyl acetate and chloroform, and acetonitrile to give 3,9-dihydro-2-methyl-3,9-dioxo-1-phenyl-2H-indeno-[2,1-c]pyridine-4-carbonitrile melting at approximately 255°–256°. The product has the formula

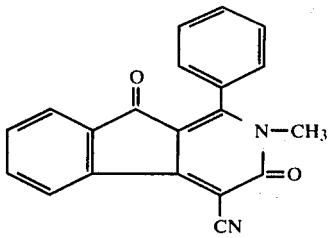

EXAMPLE 11

A mixture of 5 parts of 3,9-dihydro-3,9-dioxo-2H-indeno-[2,1-c]pyridine-4-carbonitrile, 46 parts of concentrated sulfuric acid, and 1 part of water is heated at 60°–65° for 4½ hours, then slowly diluted with 200 parts of water. The copious precipitate which forms is filtered off, washed with water, and crystallized from acetic acid to give 3,9-dihydro-3,9-dioxo-2H-indeno[2,1-c]pyridine-4-carboxamide melting above 300°. The product has the formula

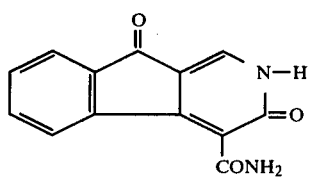

EXAMPLE 12

A mixture of approximately 2 parts of 3,9-dihydro-1-methyl-3,9-dioxo-2H-indeno[2,1-c]pyridine-4-carbonitrile, 37 parts of concentrated sulfuric acid, and 1 part of water is heated at 90°–95° for 2 hours, then slowly diluted with 175 parts of water. The precipitate which forms is filtered off, washed with methanol, dried in vacuo, and crystallized from aqueous N,N-dimethylformamide to give 3,9-dihydro-1-methyl-3,9-dioxo-2H-indeno[2,1-c]pyridine-4-carboxamide as a pale yellow solid melting above 300°. The product has the formula

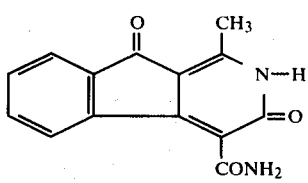

EXAMPLE 13

A mixture of 2 parts of 3,9-dihydro-1-(methylethyl)-3,9-dioxo-2H-indeno[2,1-c]pyridine-4-carbonitrile, 35 parts of concentrated sulfuric acid, and 1 part of water is heated at 90°–95° for 2 hours, then slowly diluted with 150 parts of water. The precipitate which forms is filtered off, washed with methanol, and crystallized from aqueous N,N-dimethylformamide. The product thus obtained is 3,9-dihydro-1-(methylethyl)-3,9-dioxo-2H-indeno[2,1-c]pyridiene-4-carboxamide, having the formula

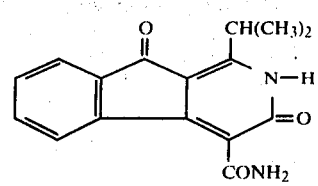

EXAMPLE 14

A mixture of 1 part of 3,9-dihydro-3,9-dioxo-1-phenyl-2H-indeno[2,1-c]pyridine-4-carbonitrile, 5 parts of potassium hydroxide, and 39 parts of 1,1-dimethylethanol is heated at the boiling point under reflux for 16 hours. The resultant mixture is diluted with 1000 parts of water, followed by sufficient acetic acid to neutralize the base present. The precipitate which forms is filtered off; consecutively washed with water, methanol, and 1,1'-oxybisethane; and dried in vacuo. The resultant yellow solid is crystallized from aqueous N,N-dimethylformamide to afford 3,9-dihydro-1-phenyl-2H-indeno[2,1-c]pyridine-4-carboxamide melting above 300°. The product has the formula

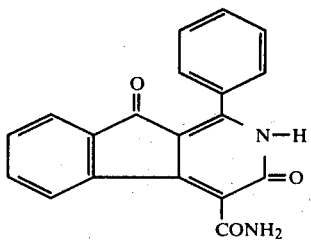

What is claimed is:
1. A compound of the formula

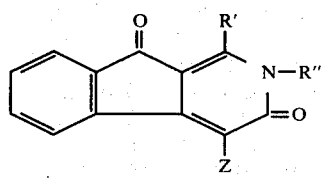

wherein R' represents hydrogen, alkyl containing fewer than 4 carbons, or phenyl; R" represents hydrogen or alkyl containing fewer than 4 carbons; and Z represents cyano or carbamoyl.

2. A compound according to claim 1 which is 3,9-dihydro-3,9-dioxo-2H-indeno[2,1-c]pyridine-4-carbonitrile.

3. A compound according to claim 1 having the formula

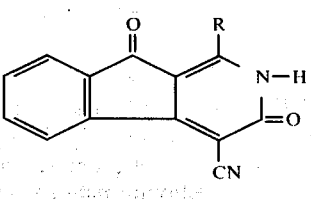

wherein R represents alkyl containing fewer than 4 carbons.

4. A compound according to claim 1 which is 3,9-dihydro-1-methyl-3,9-dioxo-2H-indeno-[2,1-c]pyridine-4-carbonitrile.

5. A compound according to claim 1 which is 3,9-dihydro-3,9-dioxo-1-phenyl-2H-indeno[2,1-c]pyridine-4-carbonitrile.

6. A compound according to claim 1 having the formula

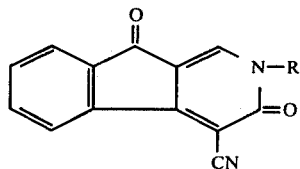

wherein R represents alkyl containing fewer than 4 carbons.

7. A compound according to claim 1 having the formula

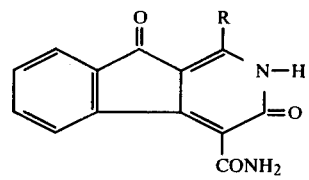

wherein R' and R" each represents alkyl containing fewer than 4 carbons.

8. A compound according to claim 1 which is 3,9-dihydro-2-methyl-3,9-dioxo-1-phenyl-2H-indeno[2,1-c]pyridine-4-carbonitrile.

9. A compound according to claim 1 which is 3,9-dihydro-3,9-dioxo-2H-indeno[2,1-c]pyridine-4-carboxamide.

10. A compound according to claim 1 having the formula wherein R represents alkyl containing fewer than 4 carbons.

11. A compound according to claim 1 which is 3,9-dihydro-1-methyl-3,9-dioxo-2H-indeno[2,1-c]pyridine-4-carboxamide.

12. A compound according to claim 1 which is 3,9-dihydro-3,9-dioxo-1,phenyl-2H-indeno[2,1-c]pyridine-4-carboxamide.

* * * * *